United States Patent [19]

Samejima et al.

[11] 4,411,933

[45] Oct. 25, 1983

[54] PROCESS FOR PREPARING ETHYLCELLULOSE MICROCAPSULES

[75] Inventors: Masayoshi Samejima, Minoh; Goichi Hirata, Yawata, both of Japan

[73] Assignee: Tanabe Seiyaku Co., Ltd., Osaka, Japan

[21] Appl. No.: 252,457

[22] Filed: Apr. 9, 1981

[30] Foreign Application Priority Data

Apr. 25, 1980 [JP] Japan ................................. 55-55808

[51] Int. Cl.³ ..................... B01J 13/02; A01N 25/28; A61K 9/62
[52] U.S. Cl. ............................... 427/213.3; 71/64.11; 71/DIG. 1; 424/19; 424/32; 424/35; 428/402.24
[58] Field of Search .......................... 252/316; 424/35

[56] References Cited

U.S. PATENT DOCUMENTS

| | | | |
|---|---|---|---|
| 3,155,590 | 11/1964 | Miller et al. | 252/316 X |
| 3,341,416 | 9/1967 | Anderson et al. | 252/316 X |
| 3,415,758 | 12/1968 | Powell et al. | 252/316 |
| 3,531,418 | 9/1970 | Fanger et al. | 252/316 |
| 3,943,063 | 3/1976 | Morishita et al. | 252/316 |
| 4,218,333 | 8/1980 | Samejima et al. | 252/316 |
| 4,220,552 | 9/1980 | Hitchcock | 252/316 |

*Primary Examiner*—Richard D. Lovering
*Attorney, Agent, or Firm*—Jordan B. Bierman; Linda Bierman

[57] ABSTRACT

A process for preparing ethylcellulose microcapsules by flocculation of the ethylcellulose is disclosed. In this process, the flocculation of the ethylcellulose is carried out in the presence of an organosilicon polymer or in the presence of said organosilicon polymer and a surfactant.

15 Claims, No Drawings

PROCESS FOR PREPARING ETHYLCELLULOSE MICROCAPSULES

This invention relates to a process for preparing ethylcellulose microcapsules.

It is known that ethylcellulose microcapsules are prepared by taking advantage of the liquid-liquid phase separation of ethylcellulose in cyclohexane. For example, Japanese Patent Publication (examined) Nos. 528/1967, 11399/1969 and 30136/1975 disclose that butyl rubber, polybutadiene, polyethylene and polyisobutylene are used as the phase-separation-inducing agent; and that said microcapsules are obtained by preparing a hot solution in cyclohexane of ethylcellulose and said phase-separation-inducing agent, dispersing particles of a core material in the solution, cooling the dispersion until the ethylcellulose separates out from the dispersion to form a liquid phase depositing on and around the particles of the core material, and then recovering the so formed capsules therefrom. However, these known methods are still unsatisfactory for industrial production of ethylcellulose microcapsules. For example, when butyl rubber, polybutadiene and polyisobutylene are used as the phase-separation-inducing agent, the removal of said agent from the microcapsules obtained can be effected only by washing the microcapsules with the large excess (e.g., 50 ml/g) of cyclohexane for a long time because of their high adhesiveness and slow velocity of dissolution in the solvent. Additionally, in making such microcapsules, as long as 4 to 10 hours are required to dissolve only one gram of butyl rubber, polybutadiene or polyisobutylene in 30 ml of cyclohexane at 78° C. This inevitably impairs the operational efficiency in making the microcapsules. On the other hand, if polyethylene is used as the phase-separation-inducing agent, said polyethylene is separated as minute particles during cooling the dispersion and deposited on and in the wall of the microcapsules. Since such minute particles of polyethylene can not be washed out completely with a poor solvent such as cyclohexane, therefore, polyethylene is not suitable for use as the phase-separation-inducing agent in making microcapsules having a particle size of less than 100μ.

As an alternative to the above-mentioned methods, U.S. Pat. No. 3,531,418 discloses a method of preparing ethylcellulose microcapsules without using a phase-separation-inducing agent, i.e., by direct flocculation of ethylcellulose induced by change of temperature. However, the ethylcellulose gel depositing on the core material by this flocculation is not viscoelastic enough to form continuous film on the surface of the core material and is still unsatisfactory to give the desired coating properties such as impermeability, flexibility, stability and so forth. Moreover, since the coating walls of the microcapsules obtained by this method becomes highly adhesive at around 50° to 65° C. by adsorbing cyclohexane or they are liable to agglomerate together into small visible lumps each containing a myriad of individual capsules, it is difficult to obtain free-flowing discrete microcapsules having uniform particle size.

As a result of various investigations, we have now found that the wall characteristics of ethylcellulose film to be formed on particles of core material can be remarkably improved and the free-flowing discrete microcapsules having uniform particle size can be readily obtained by effecting the phase separation of the ethylcellulose in the presence of an organosilicon polymer.

According to the method of the present invention, the ethylcellulose microcapsules are prepared by dissolving ethylcellulose and an organosilicon polymer in cyclohexane, dispersing particles of a core material in said solution, cooling the dispersion until ethylcellulose separates out from the dispersion to form coating walls on and around the particles of said core material, and then recovering the resultant microcapsules therefrom.

In carrying out the microencapsulation of the present invention, it is preferred to use an organosilicon polymer having a viscosity of about 50 to about 5,000,000 centistokes, especially about 100 to about 2,000,000 centistokes, at 25° C. Representative examples of the organosilicon polymer which can be used in the invention include di(lower alkyl) polysiloxane, lower alkyl phenyl polysiloxane, diphenyl polysiloxane, silicone-glycol copolymer, polystyrene-polydi(lower alkyl)-siloxane block copolymer and so forth. Among those organosilicon polymers, preferred subgenus includes, for example, dimethyl polysiloxane, methylphenyl polysiloxane, diphenyl polysiloxane, silicone-glycol copolymer, polystyrenepolydimethylsiloxane block copolymer and so forth. Alternatively, a mixture of about 99 to about 50 w/w % of such organosilicon polymer and about 1 to about 50 w/w % of additives such as silicon dioxide, titanium oxide, calcium stearate or talc may be used for the purpose of the present invention.

On the other hand, ethylcellulose having an ethoxy content of about 47 to about 55 w/w % is preferably used as the wall-forming material of the present invention. It is also preferred that the viscosity of said ethylcellulose when measured at 25° C. with respect to a 5 w/w % solution of it in toluene-ethanol (4:1) is within the range of about 3 to about 500 centipoises, especially about 40 to about 110 centipoises.

Further, the core material to be microencapsulated should be insoluble or incompatible in cyclohexane or a cyclohexane solution containing either one or both of the organosilicon polymer and ethylcellulose. Such core material may be either solid, gel or semi-solid. In order to prepare microcapsules having uniform particle size, it is preferred that the core material has a particle size of less than about 1,000μ, especially about 100 to about 450μ. Any one of pharmaceutically active compounds, agricultural chemicals, fertilizers and cosmetics may be used as the core material to be microencapsulated in the present invention. Such pharmaceutically active compounds include, for example, vitamines (e.g., ascorbic acid, thiamine hydrochloride, pyridoxine hydrochloride, calcium pantotenate, methylmethionine sulfonium chloride); amino acids (e.g., potassium aspartate, magnesium aspartate, sodium glutamate, lysine hydrochloride); peptides (e.g., glutathione); sulfa drugs (e.g., sulfamethomidine, sulfisoxazol); agents affecting circulatory organs (e.g., calcium D-(+)-4-(2,4-dihydroxy-3,3-dimethylbutyramido)butyrate hemihydrate, papaverine hydrochloride, d-3-acetoxy-cis-2,3-dihydro-5-[2-(dimethylamino)ethyl]-2-(p-methoxyphenyl)-1,3-benzothiazepin-4(5H)-one hydrochloride, reserpine); agents affecting respiratory organs (e.g., 1-1-(3,4,5-trimethoxybenzyl)-6,7-dihydroxy-1,2,3,4-tetrahydroisoquinoline hydrochloride monohydrate, N-cyclohexyl-N-methyl-(2-amino-3,5-dibromobenzyl)amine hydrochloride, tipepidine hibenzate); anti-biotics (e.g., benzylpenicillin calcium, benzylpenicillin sodium, phenoxymethylpenicillin potassium, ampicillin); anti-tumor agents (e.g., 5-fluorouracil, N-(2-tetrahydrofuryl)-5-fluorouracil, breomycine hydrochloride);

agents affecting nervous system (e.g., 1,1-dimethyl-5-methoxy-3-(dithien-2-ylmethylene)piperidinium bromide monohydrate, lidocaine hydrochloride, chloropromazine hydrochloride); agents affecting digestive organs (e.g., magnesium silicate, precipitated calcium carbonate); anti-histamics (e.g., diphenhydramine hydrochloride, chlorpheniramine maleate); analgesics (e.g., acetylsalicyclic acid, quinine hydrochloride, sulpyrine); and so forth. Fertilizers such as nitrogenous fertilizer (e.g., ammonium sulfate, ammonium chloride, ammonium nitrate, lime nitrogen); potassic fertilizer (e.g., potassium sulfate, potassium chloride); and phosphatic fertilizer (e.g., superphosphate of lime, fused phosphate fertilizer, sodium phosphate) may also be used as the core material of the invention.

In making the ethylcellulose microcapsules in accordance with the present invention, it is preferred to dissolve ethylcellulose and the organosilicon polymer in cyclohexane at about 75° to about 80° C., and then disperse therein the core material under continuous stirring at about 100 to about 600 rpm. The amount of ethylcellulose to be used may be varied within the range of about 0.02 to about 5.0 gram per gram of the core material to be used, and the wall thickness of the microcapsules can be readily adjusted by changing the quantitative ratio of said ethylcellulose to the core material within the above range. Generally, it is preferred that ethylcellulose is dissolved in cyclohexane at a concentration of about 0.1 to about 10 w/v %. On the other hand, the amount of the organosilicon polymer to be used does not depend on the amount of each one of ethylcellulose and the core material as well as the quantitative ratio of the latter two compounds used. However, it is preferred that the organosilicon polymer is dissolved in cyclohexane at a concentration of about 0.01 to about 10 w/v %, especially about 0.5 to about 5 w/v %. When the above-obtained dispersion is then cooled gradually (e.g., at a rate of about 0.05° to about 4° C., especially about one to about 2° C., per minute), ethylcellulose in the form of "gel" separates out from the dispersion at about 68° C. mainly by flocculation thereof thereby depositing on or wrapping the particles of the core material, and the ethylcellulose gel thus deposited forms seamless walls. When the temperature is further lowered to a temperature not higher than about 40° C. (e.g., 25° to 40° C.), the thus-formed embryonic microcapsules are shrunken and become solid by solvent loss from the capsule walls, thus giving stable ethylcellulose microcapsules. The microcapsules thus obtained may be recovered by conventional manners such as, for example, decantation, centrifugation, filtration and so forth. Further, the ethylcellulose microcapsules which are substantially free from the organosilicon polymer can be readily obtained by washing the thus-obtained microcapsules with cyclohexane, petroleum ether, n-hexane and so forth, i.e., with an organic solvent which dissolves the organosilicon polymer but does not dissolved both of ethylcellulose and the core material used.

According to the present invention, the ethylcellulose microcapsules may also be prepared by using the organosilicon polymer in combination with a surfactant. Namely, the ethylcellulose microcapsules are prepared by dissolving ethylcellulose, an organosilicon polymer and a surfactant in cyclohexane, dispersing particles of a core material in said solution, cooling the dispersion until the ethylcellulose separates out from the dispersion to form coating walls on and around the particles of said core material, and then recovering the resultant microcapsules therefrom. When the organosilicon polymer is used in combination with the surfactant, the wall characteristics of ethylcellulose film to be formed on particles of the core material are improved more remarkably as compared with those of the microcapsules which are obtained by the use of the organosilicon polymer alone. All of the above-mentioned operations can be carried out in the same manner as described hereinbefore. A wide variety of surfactants can be used in the present invention. For example, such surfactants include nonionic surfactants such as sorbitan fatty acid ($C_{12-18}$) ester, glycerol fatty acid ($C_{8-18}$) ester, propylene glycol fatty acid ($C_{8-18}$) ester, sucrose fatty acid ($C_{12-18}$) ester, polyoxyethylene sorbitol fatty acid ($C_{12-18}$) ester, polyoxyethylene fatty acid ($C_{12-18}$) ester, trialkyl ($C_{12-18}$) phosphate, polyoxyethylene alkyl ($C_{8-9}$)-phenyl ether and polyoxyethylenepolyoxypropylene block copolymer; anionic surfactants such as dialkyl ($C_{5-8}$) alkali metal sulfosuccinate and fatty acid ($C_{8-24}$) metal salt (i.e., metallic soap); and phospholipids. More specifically, the surfactants which can be used in the present invention include sorbitan fatty acid ($C_{12-18}$) ester such as sorbitan monolaurate, sorbitan sesquilaurate, sorbitan trilaurate, sorbitan monooleate, sorbitan sesquioleate, sorbitan monostearate; glycerol fatty acid ($C_{8-18}$) ester such as glycerol monocaprylate, glycerol monolaurate, glycerol dilaurate, glycerol monooleate; propylene glycol fatty acid ($C_{8-18}$) ester such as propylene glycol monocaprylate, propylene glycol monolaurate, propylene glycol monooleate; sucrose fatty acid ($C_{12-18}$) ester having a HLB of 1 to 6 such as a mono-, di- or tri-ester of sucrose and myristic, palmitic or stearic acid or a mixture thereof; polyoxyethylene sorbitol fatty acid ($C_{12-18}$) ester having a HLB of not higher than 6 such as polyoxyethylene sorbitol hexastearate; polyoxyethylene fatty acid ($C_{12-18}$) ester having a HLB of not higher than 6 such as polyoxyethylene monooleate; trialkyl ($C_{12-18}$) phosphate such as trioleyl phosphate, trilauryl phosphate; polyoxyethylene alkyl ($C_{8-9}$)-phenyl ether having a HLB of not higher than 6 such as polyoxyethylene nonylphenyl ether, polyoxyethylene octylphenyl ether; dialkyl ($C_{5-8}$) alkali metal sulfosuccinate such as di-n-octyl sodiumsulfosuccinate, di-n-hexyl sodiumsulfosuccinate, diamyl sodiumsulfosuccinate, bis(1-methylamyl) sodiumsulfosuccinate, bis(2-ethylhexyl) sodiumsulfosuccinate; metallic soap such as aluminium monostearate, aluminium distearate, aluminium tristearate, iron tristearate, calcium stearoyl-2-lactylate; and phospholipids such as soybean phospholipid, egg-york phospholipid, phosphatidylethanolamine, phosphatidylcholine, phosphatidylserine, inositolphosphatide. A suitable amount of the surfactant to be used may be within the range of about 0.001 to about 10 gram, especially about 0.004 to about 4 gram, per gram of the organosilicon polymer used. Generally, it is preferred that the surfactant is dissolved in cyclohexane at a concentration of about 0.003 to about 10 w/v %, especially about 0.008 to about 4 w/v %.

In the above-mentioned method of the present invention, the organosilicon polymer which may be optionally used together with the surfactant serves to increase the viscoelasticity of the ethylcellulose gel which separates out during the microencapsulation step. Such increased viscoelasticity of the ethylcellulose gel serves of course to increase the ethylcellulose gel's ability to deposit on particles of the core material and the wetability of said ethylcellulose gel thereby improving the wall characteristics of ethylcellulose gel, i.e., to form the microcapsules of compact and complete wall structure. Moreover, according to the present invention, the free-flowing discrete microcapsules of uniform particle size are obtained in a high yield because, during the cooling step, each embryonic capsules formed are protected with the adsorption layer of the organosilicon polymer (or a mixture of said organosilicon polymer and the surfactant) formed on the surface of said capsules thereby keeping them from agglomerating together into small lumps each containing a myriad of individual capsules. Further, since the microcapsules prepared in the present invention has excellent free-flowing characteristics and show no substantial agglomeration of each capsules, pharmaceutical preparations such as tablets can be prepared therefrom without deterioration in the quality of such preparations (e.g., sticking or capping in compressed tablets). In addition, according to the present invention, the microencapsulation steps can be accomplished within a shorter period of time as compared with the known methods (e.g., Japanese Patent Publication (examined) Nos. 528/1967, 11399/1969 and 30136/1975) because of the high velocity of dissolution of the organosilicon polymer in cyclohexane. For example, although it takes more than 4 hours to dissolve 3 g of polyisobutylene (viscosity average molecular weight: $7.3 \times 10^4$) in 100 ml of cyclohexane at a temperature of 78° C., each one of the organosilicon polymer and the surfactant used in the present invention can be dissolved in cyclohexane within 5 minutes under the same conditions. Further, since the flocculation of ethylcellulose in the present invention is effected with the aid of the organosilicon polymer having high velocity of dissolution in cyclohexane, the ethylcellulose microcapsules substantially free from the solvent and silicone oil are readily obtained by simple washing with cyclohexane or other suitable solvent, followed by drying thereof. Additionally, the method of the present invention is advantageous in that a large amount of the core material can be dispersed in a cyclohexane solution of the organosilicon polymer because of low viscosity of said cyclohexane solution. For example, a cyclohexane solution containing 3% of dimethyl polysiloxane has the viscosity of as low as 5 centipoises at 30° C. and, therefore, the core material can be dispersed in said cyclohexane solution at a concentration of as high as 50 w/w %. Unlike the method of the present invention, however, in the known method the core material can not be dispersed at a concentration higher than 20w/w % in a cyclohexane solution containing 3% of polyisobutylene because said solution has the viscosity of as high as 150 centipoises.

When the microencapsulation steps of the present invention is carried out by the use of organosilicon polymer in combination with a surfactant, the ethylcellulose microcapsules prepared has more excellent free-flowing characteristics and more uniform particle size as compared with the microcapsules prepared by the use of the organosilicon polymer alone because, during cooling step, each embryonic capsules formed are protected with the adsorption layer of a mixture of said organosilicon polymer and the surfactant thereby keeping them from agglomerating together.

Practical and presently-preferred embodiments of the present invention are illustratively shown in the following lines. In this specification and claims, the term "lower alkyl" should be interpreted as referring to alkyl having one to four carbon atoms.

EXPERIMENT 1

Microcapsules containing calcium hopatenate (chemical name: D-(+)-4-(2,4-dihydroxy-3,3-dimethylbutyramido)butyrate hemihydrate) were prepared in accordance with the following methods. The thus-obtained microcapsules (i.e., microcapsules which met the requirements of "Fine Granules" specified in THE PHARMACOPOEIA OF JAPAN 9th-Edition) were examined with respect to the yield and taste of said microcapsules as well as the amount of active ingredient (i.e., calcium hopatenate) contained in said microcapsules. The results are shown in Table 1.

(Preparation of Microcapsules)

(i) The method of the present invention:

12 g of silicone resin which meet the requirements specified in JAPANESE STANDARDS OF FOOD ADDITIVES 4th-Edition (said silicone resin comprises 100 parts of dimethyl polysiloxane (viscosity: 200 centistrokes at 25° C.) and 10 parts of silicon dioxide) and 16 g of soybean phospholipid were dissolved in 400 ml of cyclohexane, and 18.1 g of ethylcellulose (said ethylcellulose has the ethoxy content of 48.5 w/w %, and a 5 w/w % solution thereof in toluene-ethanol (4:1) has the viscosity of 100 centipoises at 25° C.) were dissolved therein at 78° C. under stirring. 240 g of calcium hopatenate (powder) having a particle size of 105 to 350μ were dispersed in the solution under stirring at 400 rpm. The dispersion was cooled to room temperature at a rate of about 2° C. per minute. The microcapsules thus formed were recovered by filtration, washed with cyclohexane and dried. Said microcapsules were passed through the nest of JIS (Japanese Industrial Standard) standard sieve (500μ aperture) and then the nest of JIS standard sieve (150μ aperture). The microcapsules which passed through the former sieve but did not pass through the latter sieve were collected, whereby 250 g of calcium hopatenate-containing microcapsules which met the requirements of "Fine Granules" specified in THE PHARMACOPOEIA OF JAPAN 9th-Edition were obtained.

(ii) The method of the present invention:

This method was carried out in the same manner as described in paragraph (i) except that 16 g of sucrose fatty acid ester (HLB: 3; components of fatty acid: stearic acid, palmitic acid and myristic acid; type of ester: a mixture of mono-, di- and tri-esters) were used instead of 16 g of soybean phospholipid, whereby 249 g of calcium hopatenate-containing microcapsules which met the requirements of "Fine Granules" specified in THE PHARMACOPOEIA OF JAPAN 9th-Edition were obtained.

(iii) The method of the present invention:

This method was carried out in the same manner as described in paragraph (i) except that 12 g of silicone resin were used instead of 12 g of silicone resin and 16 g of soybean phospholipid, whereby 231 g of calcium hopatenate-containing microcapsules which met the requirements of "Fine Granules" specified in THE PHARMACOPOEIA OF JAPAN 9th-Edition were obtained.

(iv) The method of Japanese Patent Publication (examined) No. 30136/1975:

18.1 g of ethylcellulose (said ethylcellulose has the ethoxy content of 48.5 w/w %, and a 5 w/w % solution thereof in toluene-ethanol (4:1) has the viscosity of 100 centipoises at 25° C.) were dissolved at 78° C. under stirring in 400 ml of a cyclohexane solution containing 3 w/w % of polyisobutylene (said polyisobutylene has the viscosity-average molecular weight of 73,000). 240 g of calcium hopatenate having a particle size of 105 to 350μ were dispersed in the solution under stirring at 400 rpm, and the dispersion was cooled to room temperature at a rate of about 2° C. per minute. The microcapsules thus formed were treated in the same manner as described in paragraph (i), whereby 208 g of calcium hopatenate-containing microcapsules which met the requirements of "Fine Granules" specified in THE PHARMACOPOEIA OF JAPAN 9th-Edition were obtained.

(v) The method of U.S. Pat. No. 3,531,418:

This method was carried out in the same manner as described in paragraph (i) except that silicone resin and soybean phospholipid were not used, whereby 103 g of calcium hopatenate-containing microcapsules which met the requirements of "Fine Granules" specified in THE PHARMACOPOEIA OF JAPAN 9th-Edition were obtained.

TABLE 1

| Methods | Yield of microcapsules (%)* | Amount of calcium hopatenate contained in microcapsules (%) | Taste of microcapsules** |
|---|---|---|---|
| (The method of the present invention) | | | |
| (i) | 97.1 | 93.1 | (−) |
| (ii) | 96.5 | 93.0 | (−) |
| (iii) | 90.6 | 94.0 | (−) |
| (The method of prior arts) | | | |
| (iv) | 85.2 | 98.1 | (++) |
| (v) | 41.7 | 97.4 | (++) |

Note:
*Yield of microcapsules was calculated according to the following formulae:
Ycalc = (b/a) × 100
Yield of microcapsules (%) = (Yobs/Ycalc) × 100 = (a/b) × Yobs
a: Amount (%) of active ingredient (i.e., calcium hopatenate) contained in microcapsules
b: Amount (g) of active ingredient used
Ycalc: Theoretic yield (g) which would be obtained if all of active ingredient used were converted into microcapsules containing a % of said active ingredient.
Yobs: Amount (g) of microcapsules which met the requirements of "Fine Granules" specified in THE PHARMACOPEIA OF JAPAN 9th-Edition.
**:
(−): tasteless
(++): strong bitter taste It can be seen from Table 1 that in the method of the present invention the microcapsules having uniform particle size were prepared in higher yield as compared with the method of prior arts. It can also be seen from Table 1 that the microcapsules prepared by the method of the present invention were tasteless and suitable for oral administration thereof because the bitter taste of active ingredient (i.e., calcium hopatenate) was masked with thicker wall film of said microcapsules than that of the microcapsules prepared by the method of prior arts.

EXPERIMENT 2

Microcapsules containing trimethoquinol hydrochloride (chemical name: 1-1-(3,4,5-trimethoxybenzyl)-6,7-dihydroxy-1,2,3,4-tetrahydroisoquinoline hydrochloride monohydrate) were prepared in accordance with the following methods. The thus-obtained microcapsules (i.e., microcapsules which met the requirements of "Fine Granules" specified in THE PHARMACOPOEIA OF JAPAN 9th-Edition) were examined with respect to the yield of said microcapsules and a period of time (i.e., 50% release time) which was necessary to release 50% of active ingredient from the microcapsules. The results are shown in Table 2.

(Preparation of Microcapsules)

(i) The method of the present invention:

18 g of silicone resin which meets the requirements specified in JAPANESE STANDARDS OF FOOD ADDITIVES 4th-Edition (said silicone resin comprises 100 parts of dimethyl polysiloxane (viscosity: 200 centistokes at 25° C.) and 10 parts of silicon dioxide) and 18 g of a surfactant (shown in Table 2) were dissolved in 600 ml of cyclohexane, and 18 g of ethylcellulose (said ethylcellulose has the ethoxy content of 48.5 w/w %, and a 5 w/w % solution thereof in toluene-ethanol (4:1) has the viscosity of 100 centipoises at 25° C.) were dissolved therein at 78° C. under stirring. 90 g of trimethoquinol hydrochloride (powder) having a particle size of 149 to 250μ were dispersed in the solution under stirring at 400 rpm. The dispersion was cooled to room temperature at a rate of about 1° C. per minute. The microcapsules thus formed were collected by filtration, washed with cyclohexane and dried. Said microcapsules were passed through the nest of JIS standard sieve (500μ aperture) and then the nest of JIS standard sieve (150μ aperture), whereby about 98 g of trimethoquinol hydrochloride-containing microcapsules which met the requirements of "Fine Granules" specified in THE PHARMACOPOEIA OF JAPAN 9th-Edition were obtained.

(ii) The method of U.S. Pat. No. 3,531,418:

18 g of ethylcellulose (said ethylcellulose has the ethoxy content of 48.5 w/w %, and a 5 w/w % solution thereof in toluene-ethanol (4:1) has the viscosity of 100 centipoises at 25° C.) were dissolved in 600 ml of cyclohexane at 78° C. under stirring. 90 g of trimethoquinol hydrochloride (powder) having a particle size of 149 to 250μ were dispersed in the solution under stirring at 400 rpm. The dispersion was cooled to room temperature at a rate of about 1° C. per minute. The microcapsules thus formed were treated in the same manner as described in paragraph (i), whereby 33 g of trimethoquinol hydrochloride-containing microcapsules which met the requirements of "Fine Granules" specified in THE PHARMACOPOEIA OF JAPAN 9th-Edition were obtained.

TABLE 2

| Surfactants | Yield of microcapsules (%)* | Amount of trimethoquinol hydrochloride contained in microcapsules (%) | 50% release time (minutes)** |
|---|---|---|---|
| (The method of the present invention) | | | |
| Sorbitan monooleate | 91.0 | 84.1 | 136 |
| Sorbitan sesquioleate | 90.6 | 84.7 | 149 |
| Sorbitan trioleate | 92.8 | 83.7 | 185 |
| Sorbitan monostearate | 93.6 | 83.4 | 160 |
| Sorbitan monolaurate | 90.8 | 85.6 | 145 |
| Calcium stearoyl-2 lactylate | 93.3 | 83.4 | 170 |
| Glycerol monolaurate | 90.0 | 84.9 | 141 |
| Glycerol trilaurate | 91.5 | 85.0 | 136 |
| Glycerol trioleate | 89.5 | 85.1 | 120 |
| Propylene glycol monolaurate | 91.6 | 84.8 | 156 |
| Sucrose fatty | 94.5 | 83.4 | 210 |

TABLE 2-continued

| Surfactants | Yield of microcapsules (%)* | Amount of trimethoquinol hydrochloride contained in microcapsules (%) | 50% release time (minutes)** |
|---|---|---|---|
| acid ester*** | | | |
| Egg-york phospholipid | 91.6 | 85.3 | 120 |
| Phosphatidyl-ethanolamine | 92.1 | 84.3 | 125 |
| (The method of U.S. Pat. No. 3,531,418) | | | |
| — | 34.9 | 95.1 | 35 |

Note:
*same as defined in the footnote of Table 1.
**The 50% release time was estimated at 37° C. in the 1st fluid (i.e., the simulated gastric fluid) specified in THE PHARMACOPOEIA OF JAPAN 9th-Edition.
***sucrose fatty acid ester (HLB: 1) comprising a mixture of mono-, di- and tri-esters of sucrose and stearic, palmitic and myristic acids

EXPERIMENT 3

18 g of dimethyl polysiloxane (viscosity: 2,000,000 centistokes at 25° C.) and 0.06 g of a surfactant (shown in Table 3) were dissolved in 600 ml of cyclohexane, and 18 of ethylcellulose (said ethylcellulose has the ethoxy content of 48.5 w/w %, and a 5 w/w % solution thereof in toluene-ethanol (4:1) has the viscosity of 100 centipoises at 25° C.) were dissolved therein at 78° C. under stirring. 90 g of ascorbic acid (powder) having a particle size of 149 to 250μ were dispersed in the solution under stirring at 300 rpm. The dispersion was cooled to room temperature at a rate of about 0.5° C. per minute. The microcapsules thus formed were collected by filtration, washed with cyclohexane and n-hexane, and then dried. Said microcapsules were treated with the JIS standard sieves (500μ aperture and 150μ aperture) in the same manner as described in Experiment 1-(i), whereby about 96 g of ascorbic acid-containing microcapsules which met the requirements of "Fine Granules" specified in THE PHARMACOPOEIA OF JAPAN 9th-Edition were obtained. The characteristics of the microcapsules obtained are shown in Table 3.

TABLE 3

| Surfactants | Yield of microcapsules (%) | Amount of ascorbic acid contained in microcapsules (%) | 50% release time (minutes)** |
|---|---|---|---|
| Sucrose fatty acid ester*** | 93.1 | 83.9 | 68 |
| Sorbitan trioleate | 90.6 | 85.6 | 57 |
| Propylene glycol monooleate | 91.0 | 85.0 | 60 |
| Di-n-hexyl sodium-sulfosuccinate | 91.5 | 84.1 | 57 |
| Soybean phospholipid | 91.7 | 84.0 | 55 |
| No addition | 88.2 | 84.9 | 55 |

Note:
*same as defined in the footnote of Table 1.
**estimated in the same manner as described in the footnote of Table 1.
***sucrose fatty acid ester (HLB: 5) comprising a mixture of mono-, di- and tri-esters of sucrose and stearic, palmitic and myristic acids.

EXPERIMENT 4

18 g of dimethyl polysiloxane (viscosity: 2,000,000 centistokes at 25° C.) were dissolved in 600 ml of cyclohexane, and 24 g of ethylcellulose (said ethylcellulose has the ethoxy content of 48.0 w/w %, and a 5 w/w % solution thereof in toluene-ethanol (4:1) has the viscosity of 100 centipoises at 25° C.) were dissolved therein at 78° C. under stirring. A core material (shown in Table 4) having a particle size of 105μ was dispersed in the solution under stirring at 400 rpm. The dispersion was cooled to room temperature at a rate of about 3° C. per minute. The microcapsules thus formed were collected, washed with cyclohexane and then dried. Said microcapsules were passed through the nest of a JIS standard sieve (350μ aperture), and microcapsules which passed through the sieve were collected therefrom. The characteristics of the microcapsules obtained are shown in Table 4.

TABLE 4

| | Core materials | | | |
|---|---|---|---|---|
| | Ammonium sulfate | Potassium chloride | Disodium phosphate (12H$_2$O) | Monosodium phosphate |
| Amount of core material (g) | 48 | 96 | 240 | 48 |
| Yield of microcapsules (%)* | 90.5 | 93.8 | 97.8 | 91.6 |
| Amount of core material contained in microcapsules (%) | 68.5 | 80.7 | 91.5 | 67.9 |
| 50% release time (minutes)** | 100 | 92 | 93 | 9.3 |

Note:
*same as defined in the footnote of Table 1 except that the microcapsules are those that passed through the JIS standard sieve (350μ aperture).
**The 50% release time was estimated at 20° C. in water.

19.2 parts of the ammonium sulfate-containing microcapsules, 7.3 parts of the potassium chloride-containing microcapsules, 23.5 parts of the disodium phosphate (12 hydrate)-containing microcapsules and 7.1 parts of the monosodium phosphate-containing microcapsules were dispersed in 50 parts of hardened oil (previously fused at 100° C.). The dispersion was granulated by the spray method, whereby a mixed fertilizer having a particle size of about 2 mm was obtained.

The mixed fertilizer obtained above was poured into water (20° C.), and a period of time which was necessary to release 50% of each one of the ingredients (i.e., core materials) from the mixed fertilizer was examined. As a result, the 50% release time of each one of the ingredients was about 30 days.

EXAMPLE 1

18 g of dimethyl polysiloxane (viscosity: 100 centistokes at 25° C.) and 0.12 g of egg-york phospholipid were dissolved in 600 ml of cyclohexane, and 24 g of ethylcellulose (said ethylcellulose has the ethoxy content of 47.5 w/w %, and a 5 w/w % solution thereof in toluene-ethanol (4:1) has the viscosity of 100 centipoises at 25° C.) were dissolved therein at 78° C. under stirring at 400 rpm. 120 g of diltiazem hydrochloride (chemical name: d-3-acetoxy-cis-2,3-dihydro-5-[2-(dimethylamino)ethyl]-2-(p-methoxyphenyl)-1,5-benzo-thiazepin-4(5H)-one hydrochloride) having a particle size of 149 to 350μ were dispersed in the solution under stirring at 400 rpm. The dispersion was cooled to room temperature at a rate of about 2° C. per minute. The microcapsules thus formed were recovered by decantation, washed with cyclohexane and n-hexane, and then dried. Said microcapsules were passed through the nest of JIS standard sieve (500μ aperture) and then through the nest of JIS standard sieve (150μ aperture), whereby 140 g of diltiazem hydrochloride-containing microcapsules which met the requirements of "Fine Granules" specified in THE PHARMACOPOEIA OF JAPAN 9th-Edition were obtained.

The characteristics of the microcapsules thus obtained are shown as follows:
- Amount of diltiazem hydrochloride contained in the microcapsules: 83.9%
- The 50% release time (estimated in the same manner as described in the footnote of Table 2) of diltiazem hydrochloride: 175 minutes

EXAMPLE 2

18 g of silicone resin (prepared by dispersing 5.4 g of silicon dioxide powder in 12.6 g of dimethyl polysiloxane (viscosity: 1,000 centistokes at 25° C.)) and 0.03 g of sorbitan trioleate were dissolved in 600 ml of cyclohexane, and 24 g of ethylcellulose (said ethylcellulose has the ethoxy content of 47.5 w/w %, and a 5 w/w % solution thereof in toluene-ethanol (4:1) has the viscosity of 100 centipoises at 25° C.) were dissolved in the solution at 78° C. under stirring at 400 rpm. 20 g of trimepidium bromide (chemical name: 1,1-dimethyl-5-methoxy-3-(dithien-2-ylmethylene)piperidium bromide monohydrate) having a particle size of 149 to 350μ were dispersed in the solution under stirring at 400 rpm. The dispersion was cooled to room temperature at a rate of about 3° C. per minute. The microcapsules thus formed were recovered by decantation, washed with cyclohexane and n-hexane, and then dried. Said microcapsules were passed through the nest of JIS standard sieves (500μ aperture and 150μ aperture), whereby 136 g of timepidium bromide-containing microcapsules which met the requirements of "Fine Granules" specified in THE PHARMACOPOEIA OF JAPAN 9th-Edition were obtained.

The characteristics of the microcapsules thus obtained are as follows:
- Amount of timepidium bromide contained in the microcapsules: 84%
- The 50% release time (estimated in the same manner as described in the footnote of Table 2) of timepidium bromide: 230 minutes

EXAMPLE 3

18 g of methylphenyl polysiloxane (viscosity: 1,000 centistokes at 25° C.), 0.12 g of egg-york phospholipid, 24 g of ethylcellulose (said ethylcellulose has the ethoxy content of 47.5 w/w %, and a 5 w/w % solution thereof in toluene-ethanol (4:1) has the viscosity of 100 centipoises at 25° C.) and 120 g of triprolidine hydrochloride (chemical name: trans-1-(4-methylphenyl)-1-(2-pyridyl)-3-pyrrolidinoprop-1-ene hydrochloride monohydrate) having a particle size of 149 to 250μ were treated in the same manner as described in Example 1. 140 g of triprolidine hydrochloride-containing microcapsules which met the requirements of "Fine Granules" specified in THE PHARMACOPOEIA OF JAPAN 9th-Edition were obtained.

The characteristics of the microcapsules thus obtained are shown as follows:
- Amount of triprolidine hydrochloride contained in the microcapsules: 83.5%.
- The 50% release time (estimated in the same manner as described in the footnote of Table 2) of triprolidine hydrochloride: 36 minutes

EXAMPLE 4

18 g of silicone resin (prepared by dispersing 5.4 g of silicon dioxide powder in 12.6 g of dimethylpolysiloxane (viscosity: 1,000 centistokes at 25° C.)), 0.10 g of phosphatidylcholine, 24 g of ethylcellulose (said ethylcellulose has the ethoxy content of 47.5 w/w %, and a 5 w/w % solution thereof in toluene-ethanol (4:1) has the viscosity of 100 centipoises at 25° C.) and sulfametomidine (chemical name: $N^1$-(6-methoxy-2-methyl-4-pyrimidinyl)sulfanilamide monohydrate) having a particle size of 149 to 350μ were treated in the same manner as described in Example 2. 138 g of sulfametomidine-containing microcapsules which met the requirements of "Fine Granules" specified in THE PHARMACOPOEIA OF JAPAN 9th-Edition were obtained.

The characteristics of the microcapsules thus obtained are shown as follows:
- Amount of sulfametomidine contained in the microcapsules: 83.4%
- The 50% release time (estimated in the same manner as described in the footnote of Table 2) of sulfamethomidine: 4.5 days

EXAMPLE 5

21 g of silicone resin (prepared by dispersing 1 g of silicon dioxide powder in 20 g of dimethyl polysiloxane (viscosity: 1,000 centistokes at 25° C.)) were dissolved in 600 ml of cyclohexane, and 18 g of ethylcellulose (said ethylcellulose has the ethoxy content of 48 w/w %, and a 5 w/w % solution thereof in toluene-ethanol (4:1) has the viscosity of 200 centipoises at 25° C. were dissolved at 78° C. under stirring at 400 rpm. 168 g of glutathione (powder) having a particle size of 149 to 350μ were dispersed in the solution under stirring at 400 rpm. The dispersion was cooled to room temperature at a rate of about 1° C. per minute. The microcapsules thus formed were recovered by filtration, washed with cyclohexane and then dried, whereby 175 g of glutathione-containing microcapsules which met the requirements of "Fine Granules" specified in THE PHARMACOPOEIA OF JAPAN 9th-Edition were obtained.

The characteristics of the microcapsules thus obtained are shown as follows:
- Amount of glutathione contained in the microcapsules: 88.9%
- The 50% release time (estimated at 37° C. in water) of glutathione: 390 minutes

EXAMPLE 6

18 g of silicone resin (prepared by dispersing 2 g of silicon dioxide powder in 16 g of dimethyl polysiloxane (viscosity: 1,000 centistokes at 25° C.)) and 6 g of aluminium monostearate were dissolved in 600 ml of cyclohexane, and 17 g of ethylcellulose (said ethylcellulose has the ethoxy content of 48.0 w/w %, and a 5 w/w % solution thereof in toluene-ethanol (4:1) has the viscosity of 100 centipoises at 25° C.) were dissolved in the solution at about 78° C. under stirring at 400 rpm. 180 g of calcium hopatenate (powder) having a particle size of 105 to 350μ were dispersed in the solution under stirring at 400 rpm. The dispersion was cooled to room temperature at a rate of about 2° C. per minute. The microcapsules thus formed were recovered by decantation, washed with cyclohexane and then dried. Said microcapsules were passed through the nest of JIS standard sieves (500μ aperture and 150μ aperture), whereby 190 g of calcium hopatenate-containing microcapsules which met the requirements of "Fine Granules" specified in THE PHARMACOPOEIA OF JAPAN 9th-Edition were obtained.

The characteristics of the microcapsules thus obtained are shown as follows:
Amount of calcium hopatenate contained in the microcapsules: 91.6%
Taste of the microcapsules: tasteless

EXAMPLE 7

18 g of silicone-glycol copolymer (viscosity: 10,000 centistokes at 25° C.), 24 g of ethylcellulose (said ethylcellulose has the ethoxy content of 47.5 w/w %, and a 5 w/w % solution thereof in toluene-ethanol (4:1) has the viscosity of 100 centipoises at 25° C.) and 120 g of diltiazem hydrochloride (powder) having a particle size of 149 to 350μ were treated in the same manner as described in Example 1. 130 g of diltiazem hydrochloride-containing microcapsules which met the requirements of "Fine Granules" specified in THE PHARMACOPOEIA OF JAPAN 9th-Edition were obtained.

The characteristics of the microcapsules thus obtained are shown as follows:
Amount of diltiazem hydrochloride contained in the microcapsules: 84.2%
The 50% release time (estimated in the same manner as described in the footnote of Table 2) of diltiazem hydrochloride: 145 minutes

EXAMPLE 8

18 g of polystyrene-polydimethylsiloxane block copolymer (viscosity: 500,000 centistokes at 25° C.), 0.12 g of egg-york phospholipid, 24 g of ethylcellulose (said ethylcellulose has the ethoxy content of 47.5 w/w %, and a 5 w/w % solution thereof in toluene-ethanol (4:1) has the viscosity of 100 centipoises at 25° C.) and 120 g of diltiazem hydrochloride (powder) having a particle size of 149 to 350μ were treated in the same manner as described in Example 1. 140 g of diltiazem hydrochloride-containing microcapsules which met the requirements of "Fine Granules" specified in THE PHARMACOPOEIA OF JAPAN 9th-Edition were obtained.

The characteristics of the microcapsules thus obtained are shown as follows:
Amount of diltiazem hydrochloride contained in the microcapsules: 83.5%

EXAMPLE 9

18 g of dimethylpolysiloxane (viscosity: 1,000,000 centistokes at 25° C.), 0.12 g of egg-york phospholipid, 24 g of ethylcellulose (said ethylcellulose has the ethoxy content of 47.5 w/w %, and a 5 w/w % solution thereof in toluene-ethanol (4:1) has the viscosity of 100 centipoises at 25° C.) and 120 g of triprolidine hydrochloride (powder) having a particle size of 149 to 250μ were treated in the same manner as described in Example 1. 140 g of triprolidine hydrochloride-containing microcapsules which met the requirements of "Fine Granules" specified in THE PHARMACOPOEIA OF JAPAN 9th-Edition were obtained.

The characteristics of the microcapsules thus obtained are shown as follows:
Amount of triprolidine hydrochloride contained in the microcapsules: 83.9%

We claim:

1. In a process for preparing ethylcellulose microcapsules comprising the steps of (i) dissolving ethylcellulose in cyclohexane, (ii) dispersing particles of a core material in said solution, (iii) cooling the dispersion until the ethylcellulose separates out from the dispersion to form coating walls on and around the particles of said core material, and then (iv) recovering the thus-formed ethylcellulose microcapsules therefrom, the improvement wherein an organosilicon polymer is dissolved in said cyclohexane in said step (i) in an amount of 0.1 to 10 w/v %, said organosilicon polymer having a viscosity of 50 to 5 million centistokes at 25° C. and said ethylcellulose being present in an amount of 0.1 to 10 w/v %.

2. The process according to claim 1 wherein said organosilicon polymer has a viscosity of about 100 to about 2,000,000 centistokes at 25° C.

3. The process according to claim 1 wherein the organosilicon polymer is selected from the group consisting of di(lower alkyl)polysiloxane, lower alkyl phenyl polysiloxane, diphenyl polysiloxane, silicone-glycol copolymer and polystyrenepolydi(lower alkyl)-siloxane block copolymer.

4. The process according to claim 1 wherein the organosilicon polymer is selected from the group consisting of dimethyl polysiloxane, methyl phenyl polysiloxane, silicone-glycol copolymer and polystyrene-polydimethylsiloxane block copolymer.

5. The process according to any one of claims 2–4 or 1 wherein said ethylcellulose has an ethoxy content of about 47 to about 55 w/w %.

6. The process according to any one of claims 2–4 or 1 wherein the organosilicon polymer is used in combination with a surfactant.

7. The process according to claim 6 wherein the surfactant is present in an amount of about 0.001 to about 10 grams per gram of the organosilicon polymer.

8. The process according to claim 6 wherein said ethylcellulose has an ethoxy content of about 47 to about 55 w/w %.

9. The process according to any one of claims 2–4 or 1 wherein the ethylcellulose and the organosilicon polymer are dissolved in cyclohexane at a temperature of about 75° to about 80° C., and the dispersion containing the core material is cooled gradually to a temperature not higher than 40° C. at a rate of about 0.05 to about 4° C. per minute.

10. The process according to claim 9 wherein said ethylcellulose has an ethoxy content of about 47 to about 55 w/w %.

11. The process according to any one of claims 2–4 or 1 wherein the core material is a pharmaceutically active compound having a particle size of not more than 1,000μ.

12. The process according to claim 11 wherein said ethylcellulose has an ethoxy content of about 47 to about 55 w/w %.

13. The process according to claim 6 wherein the ethylcellulose, the organosilicon polymer, and the surfactant are dissolved in cyclohexane at a temperature of about 75° to about 80° C., and the dispersion containing the core material is cooled gradually to a temperature not higher than 40° C. at a rate of about 0.05 to about 4° C. per minute.

14. The process according to claim 13 wherein said ethylcellulose has an ethoxy content of about 47 to about 55 w/w %.

15. The process according to claim 13 wherein the surfactant is present in an amount of about 0.001 to about 10 grams per gram of the organosilicon polymer.

* * * * *